US012678143B2

(12) United States Patent
Koshino

(10) Patent No.: US 12,678,143 B2
(45) Date of Patent: Jul. 14, 2026

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Riko Koshino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 201 days.

(21) Appl. No.: 18/322,301

(22) Filed: May 23, 2023

(65) Prior Publication Data

US 2023/0404538 A1     Dec. 21, 2023

(30) Foreign Application Priority Data

Jun. 15, 2022   (JP) ................................. 2022-096332

(51) Int. Cl.
*A61B 8/00* (2006.01)
*A61B 8/08* (2006.01)
(52) U.S. Cl.
CPC ............ *A61B 8/5223* (2013.01); *A61B 8/085* (2013.01); *A61B 8/463* (2013.01); *A61B 8/5207* (2013.01)
(58) Field of Classification Search
None
See application file for complete search history.

(56) References Cited

U.S. PATENT DOCUMENTS

2005/0267337 A1 * 12/2005 Sakai .................... G06T 7/0012
                                                   382/128
2017/0024883 A1   1/2017 Urabe et al.
2017/0273668 A1   9/2017 Matsumoto
                (Continued)

FOREIGN PATENT DOCUMENTS

EP        3 518 771 B1    9/2020
EP        3825910 A1      5/2021
                (Continued)

OTHER PUBLICATIONS

WO-2017183466-A1 translation (Year: 2017).*
                (Continued)

*Primary Examiner* — Renee C Langhals
(74) *Attorney, Agent, or Firm* — Studebaker Brackett PLLC

(57) ABSTRACT
There is provided an ultrasound diagnostic apparatus including a determination procedure memory that stores a determination procedure, a monitor and a processor, the processor identifying characteristics of the lesion part for a determination item for route selection in a plurality of branches of the determination procedure, extracting at least one ultrasound image contributing to identification of the characteristics in the plurality of branches of the determination procedure from a plurality of ultrasound images as a basis image, performing the route selection in the plurality of branches of the determination procedure by applying the identified characteristics to the determination item to determine the medical examination category or the diagnosis category of the lesion part, and displaying a route in the determination procedure in a case where the medical examination category or the diagnosis category is determined and the extracted basis image on the monitor.

20 Claims, 12 Drawing Sheets

(56)  References Cited

U.S. PATENT DOCUMENTS

| | | | | |
|---|---|---|---|---|
| 2018/0260949 A1* | 9/2018 | Kreeger | ............... | G06T 7/0016 |
| 2018/0338741 A1 | 11/2018 | Lyman et al. | | |
| 2020/0170624 A1 | 6/2020 | Noguchi et al. | | |
| 2020/0334818 A1 | 10/2020 | Igarashi et al. | | |
| 2021/0210196 A1* | 7/2021 | Ye | .......................... | G16H 30/40 |
| 2021/0212665 A1* | 7/2021 | Tsymbalenko | ....... | A61B 8/5223 |
| 2022/0318991 A1* | 10/2022 | Sperandio | ............. | G16H 30/40 |

FOREIGN PATENT DOCUMENTS

| | | | | | |
|---|---|---|---|---|---|
| JP | 2004-180987 A | 7/2004 | | | |
| JP | 2005-342028 A | 12/2005 | | | |
| JP | 2017-023347 A | 2/2017 | | | |
| JP | 2017-169793 A | 9/2017 | | | |
| JP | 2019-535346 A | 12/2019 | | | |
| JP | 2020-081742 A | 6/2020 | | | |
| JP | 2020-146455 A | 9/2020 | | | |
| KR | 102015224 B1 * | 10/2019 | ............. | G16H 50/70 |
| WO | WO-2017183466 A1 * | 10/2017 | .............. | A61B 8/08 |
| WO | WO-2022178176 A1 * | 8/2022 | ........... | A61B 5/0033 |

OTHER PUBLICATIONS

KR-102015224-B1 machine translation (Year: 2019).*
The extended European search report issued by the European Patent Office on Oct. 23, 2023, which corresponds to European Patent Application No. 23179363.9-1126 and is related to U.S. Appl. No. 18/322,301.
"Notice of Reasons for Refusal" Office Action issued in JP 2022-096332; mailed by the Japanese Patent Office on Sep. 30, 2025.

* cited by examiner

MASS

B1

MIXED PATTERN          SOLID PATTERN          U1a          U1b

CATEGORIES 3 AND 4

MASS

B1

MIXED PATTERN          SOLID PATTERN          U1m

CATEGORIES 3 AND 4          m/n

MASS          MAXIMUM DIAMETER: L1 × L2 × L3 (mm)

B1          ASPECT RATIO: D/W

MIXED PATTERN          SOLID PATTERN

CATEGORIES 3 AND 4          U1

FIG. 20

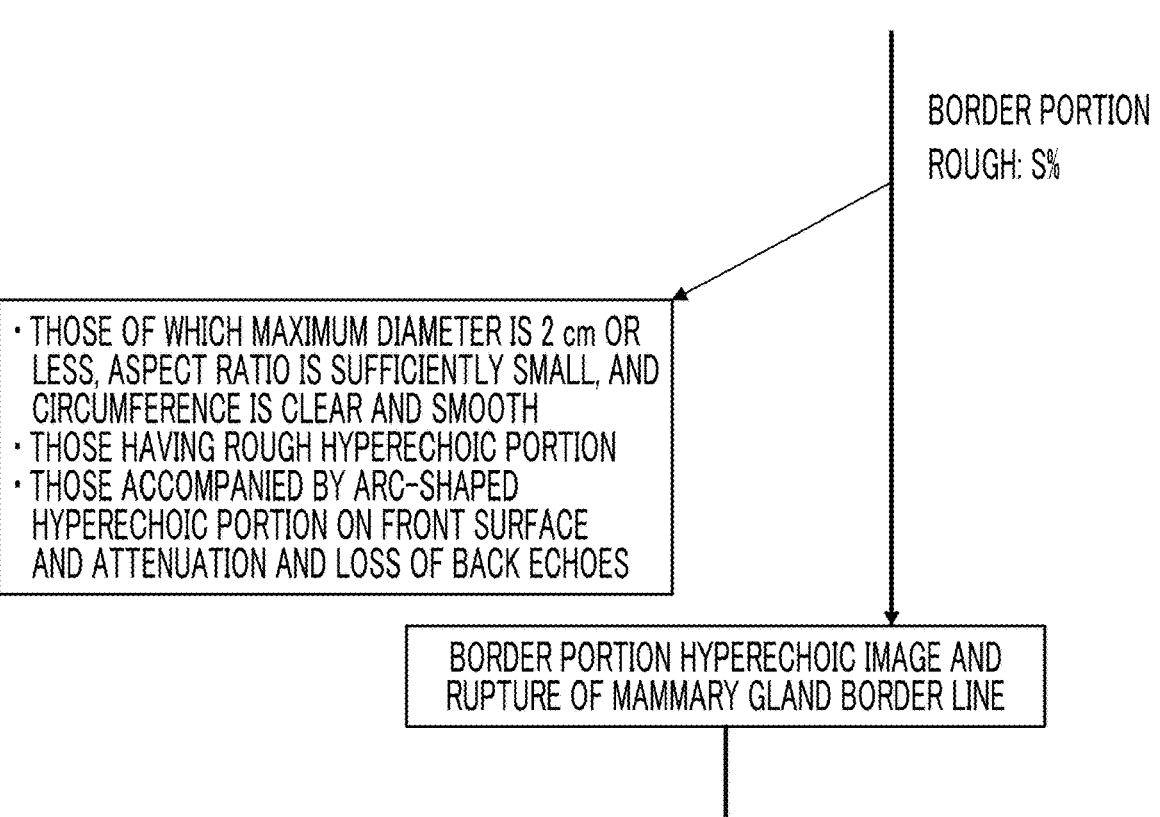

BORDER PORTION
ROUGH: S%

- THOSE OF WHICH MAXIMUM DIAMETER IS 2 cm OR LESS, ASPECT RATIO IS SUFFICIENTLY SMALL, AND CIRCUMFERENCE IS CLEAR AND SMOOTH
- THOSE HAVING ROUGH HYPERECHOIC PORTION
- THOSE ACCOMPANIED BY ARC-SHAPED HYPERECHOIC PORTION ON FRONT SURFACE AND ATTENUATION AND LOSS OF BACK ECHOES

BORDER PORTION HYPERECHOIC IMAGE AND RUPTURE OF MAMMARY GLAND BORDER LINE

FIG. 21

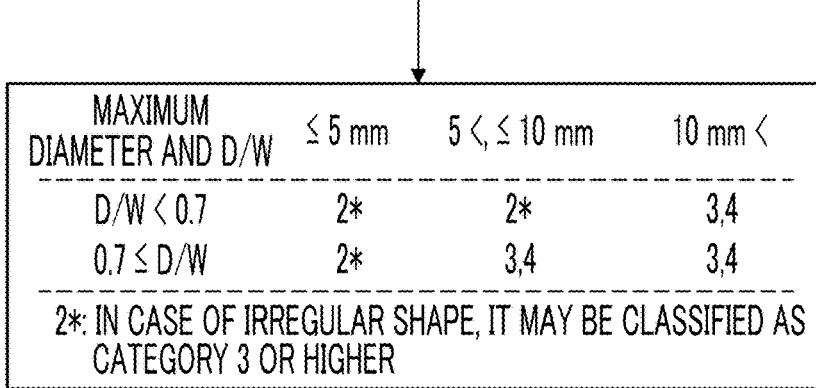

| MAXIMUM DIAMETER AND D/W | ≤ 5 mm | 5 <, ≤ 10 mm | 10 mm < |
|---|---|---|---|
| D/W < 0.7 | 2* | 2* | 3,4 |
| 0.7 ≤ D/W | 2* | 3,4 | 3,4 |

2*: IN CASE OF IRREGULAR SHAPE, IT MAY BE CLASSIFIED AS CATEGORY 3 OR HIGHER

NUMBER OF NARROW PARTS: P
NUMBER OF ANGULATED PARTS: Q

U1

MASS

B1

MIXED PATTERN          SOLID PATTERN

CATEGORIES 3 AND 4

CYSTIC PATTERN: X%
MIXED PATTERN: Y%
SOLID PATTERN: Z%

ULTRASOUND DIAGNOSTIC APPARATUS AND CONTROL METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2022-096332, filed on Jun. 15, 2022. The above application is hereby expressly incorporated by reference, in its entirety, into the present application.

BACKGROUND OF THE INVENTION

1. Field of the Invention

The present invention relates to an ultrasound diagnostic apparatus and a control method of the ultrasound diagnostic apparatus, and particularly to an ultrasound diagnostic apparatus which determines a medical examination category or a diagnosis category of a lesion part according to a predetermined determination procedure with a plurality of branches.

2. Description of the Related Art

In the related art, in the medical field, an ultrasound diagnostic apparatus using an ultrasound image has been put to practical use. In general, an ultrasound diagnostic apparatus includes an ultrasound probe with a built-in transducer array, and an apparatus main body connected to the ultrasound probe, and the ultrasound diagnostic apparatus causes the ultrasound probe to transmit an ultrasound beam toward a subject, receives an ultrasound echo from the subject by the ultrasound probe, and electrically processes a reception signal thereof to generate an ultrasound image.

JP2005-342028A discloses a device that assists an examination for a subject by determining benignancy or malignancy of a lesion part on the basis of an image such as an ultrasound image in which the lesion part of the subject is imaged.

Sequential determination options are presented according to the predetermined examination procedure, the determination is executed by referring to the information on the lesion part acquired by various tools such as a measurement tool, and the history of each determination is displayed with a thick line on the diagram in which the entire examination procedure is illustrated in a tree form. Furthermore, the information on the measurement value or the like of the lesion part which is acquired by the tool and serves as the basis of the determination is displayed corresponding to each determination.

SUMMARY OF THE INVENTION

However, in order to determine the benignancy or malignancy of the lesion part, a plurality of ultrasound images represented as a video are referred to in many cases, and in this case, there is a possibility that the basis of the determination cannot be accurately understood even in a case where the information on the measurement value or the like of the lesion part is displayed together with the history of the determination.

The present invention has been made in order to solve the problems in the related art, and an object thereof is to provide an ultrasound diagnostic apparatus and a control method of the ultrasound diagnostic apparatus which can determine a medical examination category or a diagnosis category of a lesion part and accurately understand the basis of the determination by referring to a plurality of ultrasound images.

According to the following configuration, the above object can be achieved.

[1] An ultrasound diagnostic apparatus that determines a medical examination category or a diagnosis category of a lesion part according to a predetermined determination procedure having a plurality of branches, the ultrasound diagnostic apparatus comprising:

a determination procedure memory that stores the determination procedure;

an identification unit that identifies characteristics of the lesion part for a determination item for route selection in the plurality of branches of the determination procedure stored in the determination procedure memory on the basis of a plurality of ultrasound images in which the same lesion part is imaged;

an extraction unit that extracts at least one ultrasound image contributing to identification of the characteristics in the plurality of branches of the determination procedure by the identification unit, from the plurality of ultrasound images as a basis image;

a determination unit that performs the route selection in the plurality of branches of the determination procedure by applying the characteristics identified by the identification unit to the determination item to determine the medical examination category or the diagnosis category of the lesion part;

a monitor; and a display controller that displays a route in the determination procedure in a case where the medical examination category or the diagnosis category is determined by the determination unit and the basis image extracted by the extraction unit on the monitor.

[2] The ultrasound diagnostic apparatus described in [1], in which the plurality of ultrasound images are images forming a video in which the lesion part is imaged.

[3] The ultrasound diagnostic apparatus described in [1] or [2], in which each of the plurality of ultrasound images is an image in which an entire or a part of the lesion part is imaged.

[4] The ultrasound diagnostic apparatus described in [2] or [3], in which the plurality of ultrasound images are a thinned-out image, an interpolated image, or a synthesized image from the images forming the video in which the lesion part is imaged.

[5] The ultrasound diagnostic apparatus described in any one of [1] to [4], in which the extraction unit forms an enclosing line surrounding a portion contributing to the identification of the characteristics by the identification unit, in the basis image, and the display controller superimposes and displays the enclosing line on the basis image.

[6] The ultrasound diagnostic apparatus described in any one of [1] to [5], in which the extraction unit forms a heat map in which a contribution rate of a portion contributing to the identification of the characteristics by the identification unit is represented by color shading or color difference, on the basis of the basis image, and the display controller displays the heat map on the monitor.

[7] The ultrasound diagnostic apparatus described in any one of [1] to [6], in which in a case where a plurality of the basis images are extracted for one of the branches by the extraction unit, the display controller displays the plurality of basis images side by side on the monitor.

[8] The ultrasound diagnostic apparatus described in any one of [1] to [7] further comprising an input device for a user to perform an input operation, in which in a case where a plurality of the basis images are extracted for one of the branches by the extraction unit, the display controller sequentially displays the plurality of basis images on the monitor on the basis of the input operation of the user via the input device.

[9] The ultrasound diagnostic apparatus described in [8], in which the display controller displays a page number indicating which of the plurality of basis images is the basis image being displayed on the monitor in an overlaid manner on the basis image.

[10] The ultrasound diagnostic apparatus described in any one of [1] to [9], in which the identification unit measures a size of the lesion part, and the display controller displays the size measured by the identification unit on the monitor.

[11] The ultrasound diagnostic apparatus described in any one of [1] to [10], in which the identification unit calculates a ratio of a region where the identified characteristics appear to an entire region of the lesion part for each determination item, and the display controller displays the ratio calculated by the identification unit on the monitor.

[12] The ultrasound diagnostic apparatus described in any one of [1] to [11], in which the determination unit includes a probability calculation unit that calculates a probability of the route selection in the plurality of branches of the determination procedure on the basis of the characteristics of the lesion part, and the display controller displays the probability calculated by the probability calculation unit on the monitor.

[13] The ultrasound diagnostic apparatus described in [12], in which in a case where a plurality of the medical examination categories or the diagnosis categories correspond to any one of the plurality of branches of the determination procedure, the determination unit compares the probability calculated by the probability calculation unit with a predetermined threshold value to determine the medical examination category or the diagnosis category of the lesion part.

[14] The ultrasound diagnostic apparatus described in any one of [1] to [13], further comprising: an ultrasound probe; and an image generation unit that generates the plurality of ultrasound images in which the same lesion part is imaged, by performing transmission and reception of ultrasound beams with respect to a subject using the ultrasound probe.

[15] A control method of an ultrasound diagnostic apparatus that determines a medical examination category or a diagnosis category of a lesion part according to a predetermined determination procedure having a plurality of branches, the control method comprising:

a step of identifying characteristics of the lesion part for a determination item for route selection in the plurality of branches of the determination procedure on the basis of a plurality of ultrasound images in which the same lesion part is imaged;

a step of extracting at least one ultrasound image contributing to identification of the characteristics from the plurality of ultrasound images as a basis image;

a step of performing the route selection in the plurality of branches by applying the identified characteristics to the determination item to determine the medical examination category or the diagnosis category of the lesion part; and a step of displaying a route in the determination procedure in a case where the medical examination category or the diagnosis category is determined and the extracted basis image on the monitor.

According to the present invention, characteristics of the lesion part for a determination item for route selection in the plurality of branches of the determination procedure stored in the determination procedure memory are identified by the identification unit on the basis of a plurality of ultrasound images in which the same lesion part is imaged, at least one ultrasound image contributing to identification of the characteristics in the plurality of branches of the determination procedure by the identification unit is extracted by the extraction unit from the plurality of ultrasound images as a basis image, a route in the determination procedure in a case where the medical examination category or the diagnosis category is determined and the basis image extracted by the extraction unit are displayed on the monitor. Therefore, it is possible to determine the medical examination category or the diagnosis category of the lesion part and accurately understand the basis for the determination by referring to the plurality of ultrasound images.

BRIEF DESCRIPTION OF THE DRAWINGS

FIG. 20 is a diagram illustrating a part of a determination procedure in which a ratio of a region, where characteristics of an identified lesion part are shown, to a total region of the lesion part is displayed.

FIG. 21 is a diagram illustrating a part of a determination procedure in which the numbers of "narrow parts" and "angulated parts" are displayed.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
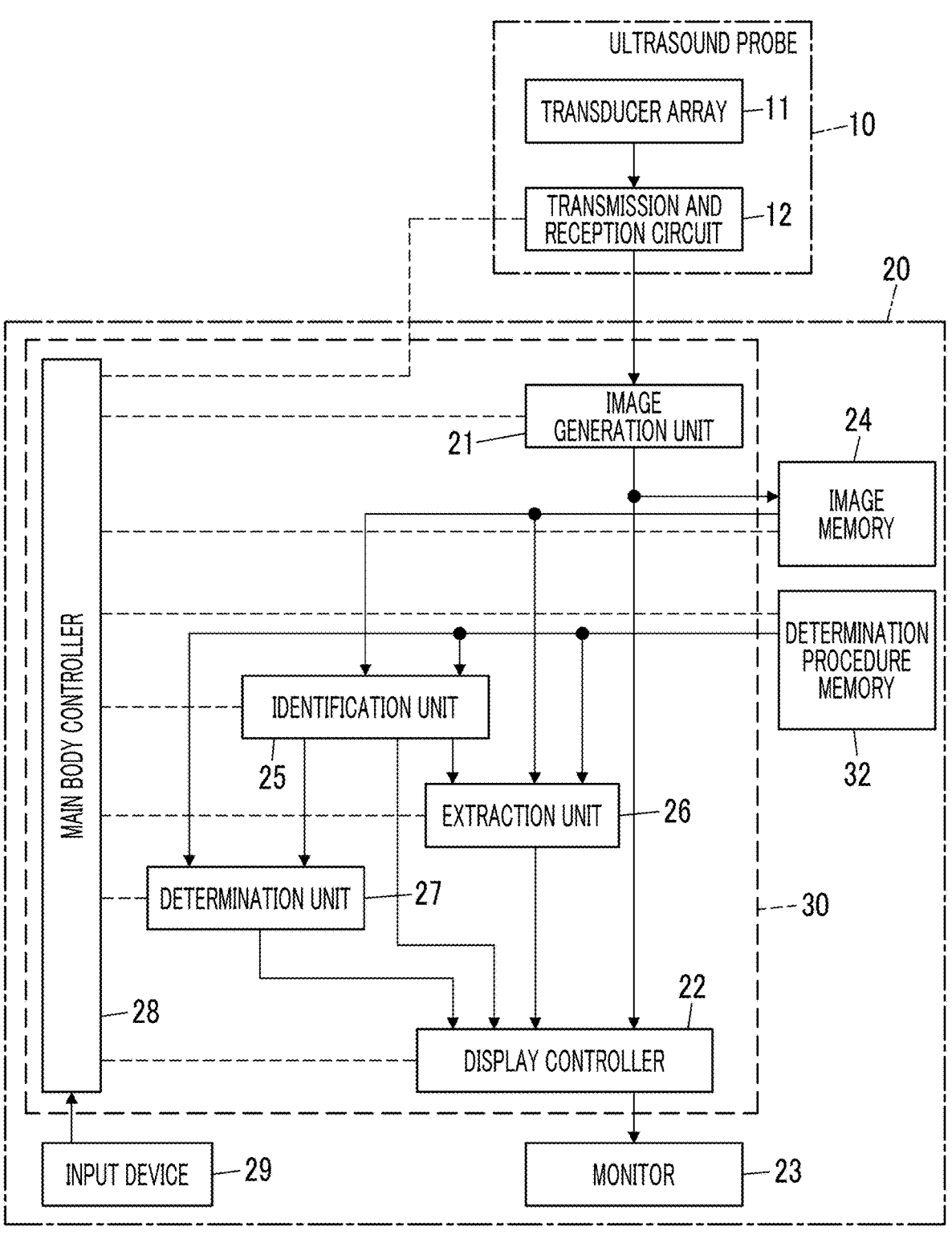
FIG. 1 is a block diagram illustrating a configuration of an ultrasound diagnostic apparatus according to a first embodiment of the present invention.

FIG. 1 illustrates a configuration of an ultrasound diagnostic apparatus according to a first embodiment of the present invention. The ultrasound diagnostic apparatus includes an ultrasound probe 10 and an apparatus main body 20. The ultrasound probe 10 and the apparatus main body 20 are connected to each other in a wired manner via a cable (not illustrated).

The ultrasound probe 10 includes a transducer array 11, and a transmission and reception circuit 12 is connected to the transducer array 11.

The apparatus main body 20 has an image generation unit 21 connected to the transmission and reception circuit 12 of the ultrasound probe 10, a display controller 22 and a monitor 23 are sequentially connected to the image generation unit 21, and an image memory 24 is connected to the image generation unit 21.

Each of an identification unit 25 and an extraction unit 26 is connected to the image memory 24, and the extraction unit 26 is connected to the identification unit 25. Further, a determination unit 27 is connected to the identification unit 25, and each of the identification unit 25, the extraction unit 26, and the determination unit 27 is connected to the display controller 22. A determination procedure memory 32 is connected to the identification unit 25, the extraction unit 26, and the determination unit 27.

A main body controller 28 is connected to the image generation unit 21, the display controller 22, the image memory 24, the identification unit 25, the extraction unit 26, the determination unit 27, and the determination procedure memory 32, and an input device 29 is connected to the main body controller 28. The transmission and reception circuit 12 of the ultrasound probe 10 is connected to the main body controller 28.

The image generation unit 21, the display controller 22, the identification unit 25, the extraction unit 26, the determination unit 27, and the main body controller 28 constitute a processor 30.

The transducer array 11 of the ultrasound probe 10 has a plurality of ultrasonic transducers arranged in a one-dimensional or two-dimensional manner. According to a drive signal supplied from the transmission and reception circuit 12, each of the transducers transmits an ultrasonic wave and receives a reflected wave from the subject to output an analog reception signal. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
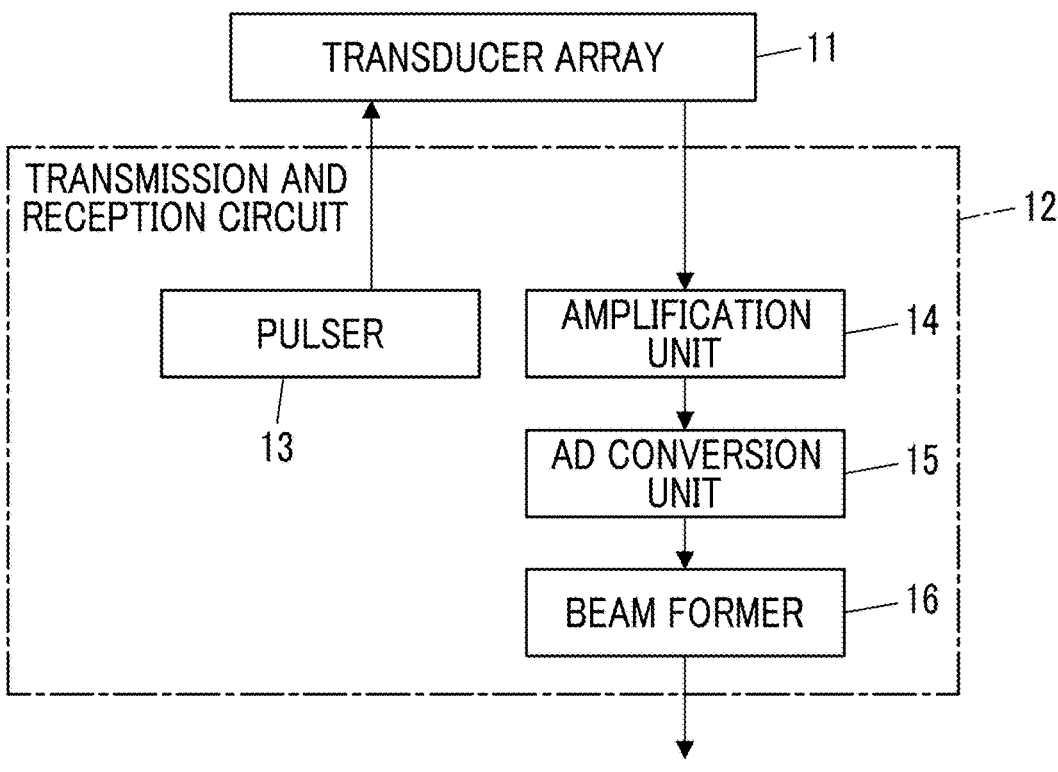
FIG. 2 is a block diagram illustrating an internal configuration of a transmission and reception circuit in the first embodiment.

The transmission and reception circuit 12 causes the transducer array 11 to transmit the ultrasonic wave and generates a sound ray signal on the basis of a reception signal acquired by the transducer array 11, under the control of the main body controller 28. As illustrated in FIG. 2, the transmission and reception circuit 12 has a pulser 13 connected to the transducer array 11, and an amplification unit 14, an analog digital (AD) conversion unit 15, and a beam former 16 that are sequentially connected in series to the transducer array 11.

The pulser 13 includes, for example, a plurality of pulse generators, and the pulser 13 adjusts the amount of delay of each drive signal so that ultrasonic waves transmitted from the plurality of transducers of the transducer array 11 form an ultrasound beam on the basis of a transmission delay pattern selected according to the control signal from the main body controller 28, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and the ultrasound echo propagates toward the transducer array 11 of the ultrasound probe 10. The ultrasound echo propagating toward the transducer array 11 in this manner is received by each transducer constituting the transducer array 11. In this case, each transducer constituting the transducer array 11 expands and contracts by receiving the propagating ultrasound echo to generate a reception signal that is an electric signal, and outputs the reception signal to the amplification unit 14.

The amplification unit 14 amplifies the signals input from each transducer constituting the transducer array 11, and transmits the amplified signals to the AD conversion unit 15. The AD conversion unit 15 converts the signal transmitted from the amplification unit 14 into digital reception data, and transmits the reception data to the beam former 16. The beam former 16 performs so-called reception focusing processing in which addition is performed by giving delays to respective pieces of the reception data converted by the AD conversion unit 15 according to a sound speed distribution or a sound speed set on the basis of a reception delay pattern selected according to the control signal from the main body controller 28. Through the reception focusing processing, a sound ray signal in which each piece of the reception data converted by the AD conversion unit 15 is phased and added and the focus of the ultrasound echo is narrowed is acquired.

Figure 3:
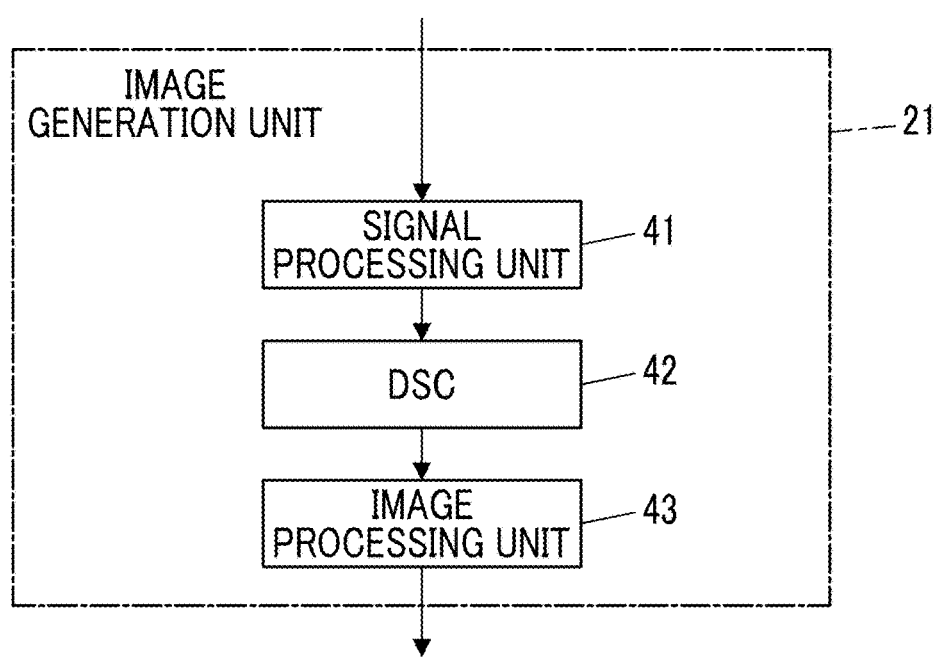
FIG. 3 is a block diagram illustrating an internal configuration of an image generation unit in the first embodiment.

As illustrated in FIG. 3, the image generation unit 21 of the apparatus main body 20 has a configuration in which a signal processing unit 41, a digital scan converter (DSC) 42, and an image processing unit 43 are sequentially connected in series.

The signal processing unit 41 generates an ultrasound image signal (B-mode image signal), which is tomographic image information regarding tissues inside the subject, by performing, on the sound ray signal sent from the transmission and reception circuit 12 of the ultrasound probe 10, correction of the attenuation due to the distance according to the depth of the reflection position of the ultrasonic wave and then performing envelope detection processing.

The DSC 42 converts (raster conversion) the ultrasound image signal generated by the signal processing unit 41 into an image signal according to a normal television signal scanning method.

The image processing unit 43 performs various kinds of necessary image processing such as gradation processing on the ultrasound image signal input from the DSC 42, and then outputs the signal representing the ultrasound image to the display controller 22 and the image memory 24. The signal representing the ultrasound image generated by the image generation unit 21 in this manner is simply referred to as an ultrasound image.

The image memory 24 is a memory that stores the ultrasound image generated by the image generation unit 21 under the control of the main body controller 28. For example, the image memory 24 can hold the ultrasound images of a plurality of frames, which are generated by the image generation unit 21, corresponding to the diagnosis for the breast of the subject.

Here, as the image memory 24, recording media such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), or the like can be used.

Figure 4:
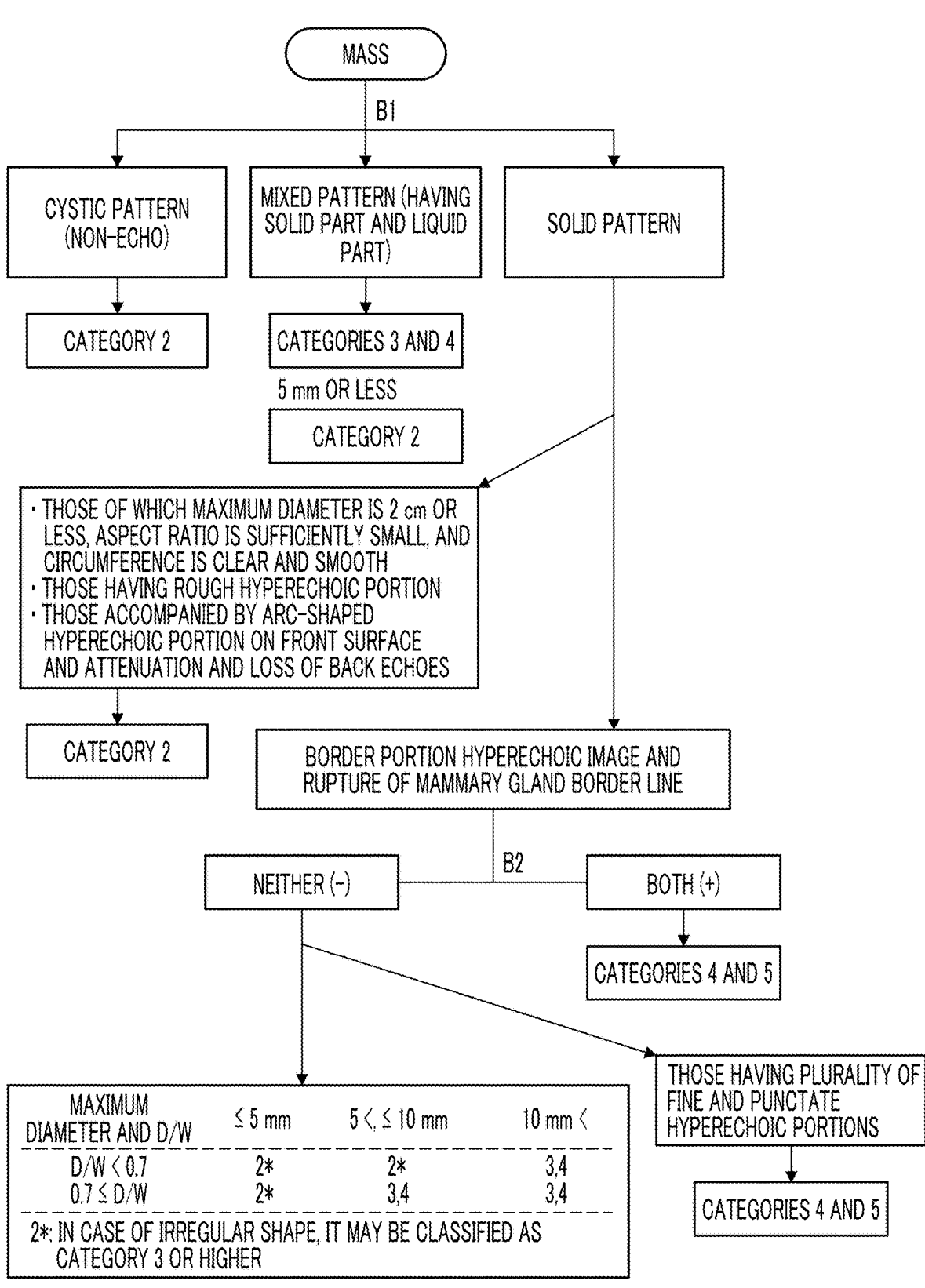
FIG. 4 is a diagram illustrating a determination procedure used in the first embodiment.

The determination procedure memory 32 is a memory that stores a predetermined determination procedure for determining which one of a plurality of standardized medical examination categories does the patient fall into on the basis of the benignancy or malignancy of the lesion part. For example, as illustrated in FIG. 4, the determination procedure for determining the medical examination category of a mass formed in the mammary glands is stored in the determination procedure memory 32. The determination procedure is shown in the guideline created by the Japanese Association of Breast and Thyroid Sonology (JABTS), and has a plurality of branches in which the route is divided according to each determination item.

As the determination procedure memory 32, for example, a flash memory, an HDD, an SSD, an FD, an MO disc, an MT, a RAM, a CD, a DVD, an SD card, and a USB memory can be used.

JABTS defines medical examination categories 1 to 5 as follows.

Medical examination category 1: no abnormal findings
Medical examination category 2: there are findings but detailed examination is not required Medical examination category 3: benign but malignancy cannot be ruled out
Medical examination category 4: suspicious of malignancy
Medical examination category 5: malignant For example, in a first branch B1, three determination items of a cystic pattern (non-echo), a mixed pattern (having a solid part and a liquid part), and a solid pattern are set regarding ultrasound echoes from the mass inside in the ultrasound image.

Then, in a case where the cystic pattern is selected on the basis of the characteristics of the ultrasound echoes, it is determined that the mass belongs to the medical examination category 2, and in a case where the mixed pattern is selected, it is determined that the mass belongs to the medical examination categories 3 and 4, but it is determined that the tumor belongs to the medical examination category 2 in a case where the maximum diameter of the tumor is 5 mm or less.

In the branch B1, in a case where the solid pattern is selected, in a case of corresponding to "the maximum diameter is 2 cm or less, the aspect ratio is sufficiently small, and the circumference is clear and smooth" or the like according to the characteristics of the ultrasound echo, it is determined that the tumor belongs to the medical examination category 2, and in a case of not corresponding thereto, the determination proceeds to a next branch B2.

In the branch B2, a border portion hyperechoic image and the rupture of the mammary gland border line are set as the determination items, in a case of corresponding to at least one of the border portion hyperechoic image or the rupture of the mammary gland border line, it is determined that the mass belongs to medical examination categories 4 and 5. In a case of corresponding to neither the border portion hyperechoic image nor the rupture of the mammary gland border line, the medical examination category is determined according to whether or not there are a plurality of fine and punctate hyperechoic portions, and according to the maximum diameter of the tumor and the aspect ratio of the mass. Furthermore, the medical examination categories may be adjusted depending on the shape of the mass.

Figures 5, 6, 7, 8, 9, 10, 11:
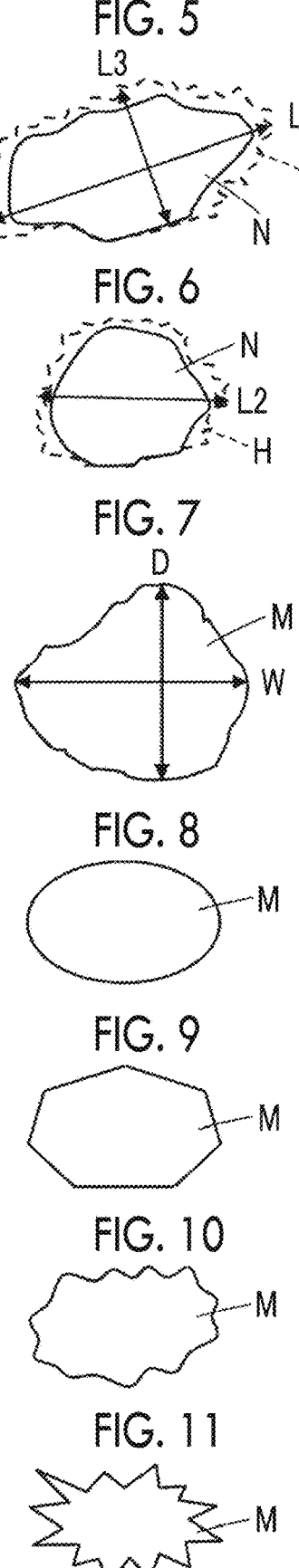
FIG. 5 is a diagram illustrating a maximum diameter of a lesion part measured by a measurement unit in one cross section.
FIG. 6 is a diagram illustrating a maximum diameter of a lesion part measured by a measurement unit in another cross section.
FIG. 7 is a diagram illustrating an aspect ratio of a lesion part measured by a measurement unit.
FIG. 8 is a diagram schematically illustrating a lesion part having an oval shape.
FIG. 9 is a diagram schematically illustrating a lesion part having a polygonal shape.
FIG. 10 is a diagram schematically illustrating a lesion part having a lobulated shape.
FIG. 11 is a diagram schematically illustrating a lesion part having an irregular shape.

Here, for example, the diameter of the tumor is expressed as L1×L2×L3 [mm] by measuring a maximum length L1 of a tumor N and a maximum width L3 on a line orthogonal to the maximum length L1 in a cross section including the maximum dimension of the tumor N as illustrated in FIG. 5, and further measuring a maximum diameter L2 in a cross section orthogonal to the cross section including the maximum dimension of the tumor N as illustrated in FIG. 6. These maximum length L1, maximum diameter L2, and maximum width L3 are measured including a border hyperechoic portion H.

The aspect ratio of the mass can be expressed as a value obtained by measuring a horizontal diameter W of a mass M in a direction parallel to the body surface (skin) of the subject and a vertical diameter D in a direction orthogonal to the horizontal diameter W without including the border hyperechoic portion, for example, as illustrated in FIG. 7, and dividing the vertical diameter D by the horizontal diameter W.

Further, for example, the shape of the mass is classified into a circular shape or oval shape (without narrow part, without angulated part) as illustrated in FIG. 8, a polygonal shape (without narrow part, with angulated part) as illustrated in FIG. 9, a lobulated shape (with narrow part, without angulated part) as illustrated in FIG. 10, and an irregular shape (with narrow part, with angulated part) as illustrated in FIG. 11, according to whether or not the shape including the border hyperechoic portion has a "narrow part" and an "angulated part".

The identification unit 25 identifies the characteristics of the lesion part for the determination items for the route selection in the plurality of branches of the determination procedure as illustrated in FIG. 4 by reading out the determination procedure from the determination procedure memory 32 and analyzing the plurality of ultrasound images that are generated by the image generation unit 21 and are stored in the image memory 24. The "cystic pattern", the "mixed pattern", the "solid pattern", the "border portion hyperechoic image", the "rupture of the mammary gland border line", the "fine and punctate hyperechoic portions", the "maximum diameter of the tumor", the "aspect ratio of the mass", the "shape of the mass", the "narrow part", the "angulated part", and the like which are exemplified in the determination procedure described above correspond to the characteristics of the lesion part to be identified by the identification unit 25.

The identification of the characteristics of the lesion part in the identification unit 25 can be executed by using at least one of template matching, an image analysis technique using feature amounts such as Adaptive Boosting (Adaboost), support vector machines (SVM), or scale-invariant feature transform (SIFT), or a determination model trained using a machine learning technique such as deep learning. The determination model is a trained model that is trained using learning ultrasound images of the breast including a lesion region, for example.

By the identification unit 25, the border of the lesion part is determined, and the size such as the maximum diameter and the aspect ratio of the lesion part is measured on the basis of the border.

The plurality of ultrasound images to be analyzed by the identification unit 25 may form a video in which the same lesion part of the subject is imaged, and each of the plurality of ultrasound images is an image in which the entire or a part of the lesion part is imaged.

The identification unit 25 may analyze the plurality of ultrasound images forming the video in which the lesion part is imaged as it is, or can analyze an image thinned out of the plurality of ultrasound images forming the video, an image interpolated with respect to the plurality of ultrasound images forming the video, or an image synthesized from the plurality of ultrasound images forming the video.

The identification result of the characteristics of the lesion part by the identification unit 25 is sent from the identification unit 25 to the extraction unit 26 and the determination unit 27.

The extraction unit 26 receives the identification result of the characteristics of the lesion part from the identification unit 25, and extracts, as the basis image, at least one ultrasound image contributing to the identification of the characteristics in the plurality of branches of the determination procedure by the identification unit 25, from the plurality of ultrasound images that are generated by the image generation unit 21 and stored in the image memory 24. That is, in the plurality of branches of the determination procedure illustrated in FIG. 4, in a case of determining whether or not the characteristics of the lesion part correspond to the determination item, the ultrasound image that best represents the determination, that is, the ultrasound image that is a decisive factor for the determination is extracted.

In this case, for example, the likelihood of determining each characteristic corresponding to the branch of the determination procedure is scored and recorded for the plurality of ultrasound images, the characteristic with the highest score or the characteristic with the highest mean, median, or mode of the scores of the plurality of ultrasound images is selected as a branch route, and the ultrasound image with the highest score of the characteristic corresponding to the selected route is extracted as the basis image.

The number of extracted ultrasound images is not limited to one, and the extraction unit 26 can extract a plurality of ultrasound images as the basis image.

The determination unit 27 receives the identification result of the characteristics of the lesion part from the identification unit 25, performs the route selection of the determination procedure by applying the characteristics of the lesion part identified by the identification unit 25 to the determination item corresponding to each branch in the plurality of branches of the determination procedure stored in the determination procedure memory 32, and thereby determines the medical examination category of the lesion part.

The display controller 22 performs predetermined processing on the ultrasound image sent from the image generation unit 21, and displays the ultrasound image on the monitor 23, under the control of the main body controller 28.

Further, the display controller 22 displays the determination procedure stored in the determination procedure memory 32 on the monitor 23, and displays the route in the determination procedure in a case of determining the medical examination category by the determination unit 27 and the basis image extracted by the extraction unit 26 on the monitor 23 by superimposing the route and the basis image on the determination procedure.

The monitor 23 is for displaying the ultrasound image, the determination procedure, and the like under the control of the display controller 22, and includes a display device such as a liquid crystal display (LCD), or an organic electroluminescence (EL) display.

The main body controller 28 controls each unit of the apparatus main body 20 and the transmission and reception circuit 12 of the ultrasound probe 10 on the basis of a control program and the like stored in advance.

Although not illustrated, a main body-side storage unit is connected to the main body controller 28. The main body-side storage unit stores a control program and the. As the main body-side storage unit, for example, a flash memory, a RAM, an SD card, an SSD, and the like can be used.

The input device 29 is for a user to perform an input operation, and is configured by, for example, a device such as a keyboard, a mouse, a trackball, a touchpad, and a touch sensor superimposed on the monitor 23.

The processor 30 having the image generation unit 21, the display controller 22, the identification unit 25, the extraction unit 26, the determination unit 27, and the main body controller 28 is configured by a central processing unit (CPU) and a control program for causing the CPU to execute various kinds of processing, but the processor 30 may be configured by using a field programmable gate array (FPGA), a digital signal processor (DSP), an application specific integrated circuit (ASIC), a graphics processing unit (GPU), or other integrated circuits (IC) or may be configured by a combination thereof.

Further, the image generation unit 21, the display controller 22, the identification unit 25, the extraction unit 26, the determination unit 27, and the main body controller 28 of the processor 30 can also be configured by being integrated partially or entirely into one CPU or the like.

Figure 12:
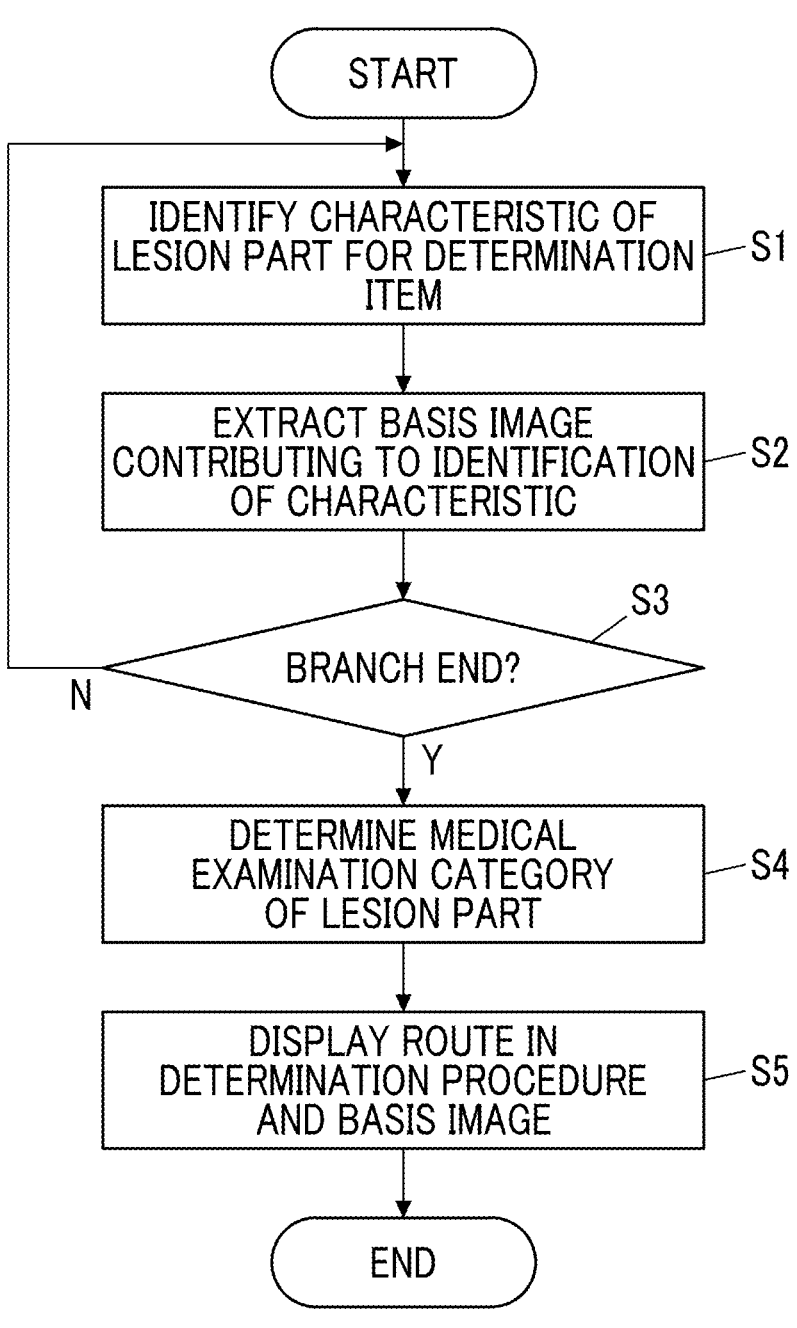
FIG. 12 is a flowchart illustrating an operation of the first embodiment.

Next, the operation of the ultrasound diagnostic apparatus according to the first embodiment will be described with reference to the flowchart illustrated in FIG. 12.

First, in Step S1, by the identification unit 25, the determination procedure is read out from the determination procedure memory 32, the plurality of ultrasound images in which the same lesion part of the subject is imaged and which are stored in the image memory 24 are analyzed, and the characteristics of the lesion part for the determination item set in each branch of the determination procedure are identified.

For example, it is determined whether the lesion part corresponds to one of three determination items set in the first branch B1 of the determination procedure illustrated in FIG. 4, that is, the cystic pattern, the mixed pattern, or the solid pattern.

Next, in Step S2, by the extraction unit 26, the determination procedure is read out from the determination procedure memory 32, and at least one ultrasound image contributing to the identification of the characteristics of the lesion part in the plurality of branches of the determination procedure performed in Step S1 is extracted as the basis image. in a case of determining whether or not the characteristics of the lesion part correspond to the determination item, the extraction unit 26 extracts the ultrasound image that best represents the determination as the basis image from the plurality of ultrasound images which are analyzed by the identification unit 25 in Step S1.

For example, the likelihood of determining each characteristic corresponding to the branch of the determination procedure is scored for the plurality of ultrasound images, the characteristic with the highest score or the characteristic with the highest mean, median, or mode of the scores of the plurality of ultrasound images is selected as a branch route, and the ultrasound image with the highest score of the characteristic corresponding to the selected route is extracted as the basis image.

In a case where there are a plurality of ultrasound images most contributing to the identification by the identification unit 25, the basis image is not limited to one ultrasound image, and a plurality of ultrasound images are extracted as the basis image.

In a case where the basis image is extracted, the processing proceeds to Step S3, and it is determined whether or not the identification of the characteristics of the lesion part in Step S1 and the extraction of the basis image in Step S2 are ended for all of the plurality of branches of the determination procedure.

In a case where there remains a branch for which the identification of the characteristics of the lesion part and the extraction of the basis image are not performed, the processing returns to Step S1, and for the next branch in the determination procedure, the identification of the characteristics of the lesion part is performed by the identification unit 25, and the extraction of the basis image is performed by the extraction unit 26 in Step S2.

In this manner, Steps S1 to S3 are repeated until identification of the characteristics of the lesion part and the extraction of the basis image are ended for all the branches in Step S3.

Then, in a case where it is determined in Step S3 that the identification of the characteristics of the lesion part and the extraction of the basis image are ended for all the branches, the processing proceeds to Step S4, and by the determination unit 27, the determination procedure is read out from the determination procedure memory 32, and the medical examination category of the lesion part is determined according to the determination procedure. In this case, the determination unit 27 can perform the route selection of the determination procedure by applying the characteristics of the lesion part identified by the identification unit 25 to the determination item corresponding to each branch in the plurality of branches of the determination procedure, and thereby determine the medical examination category of the lesion part.

Figure 13:
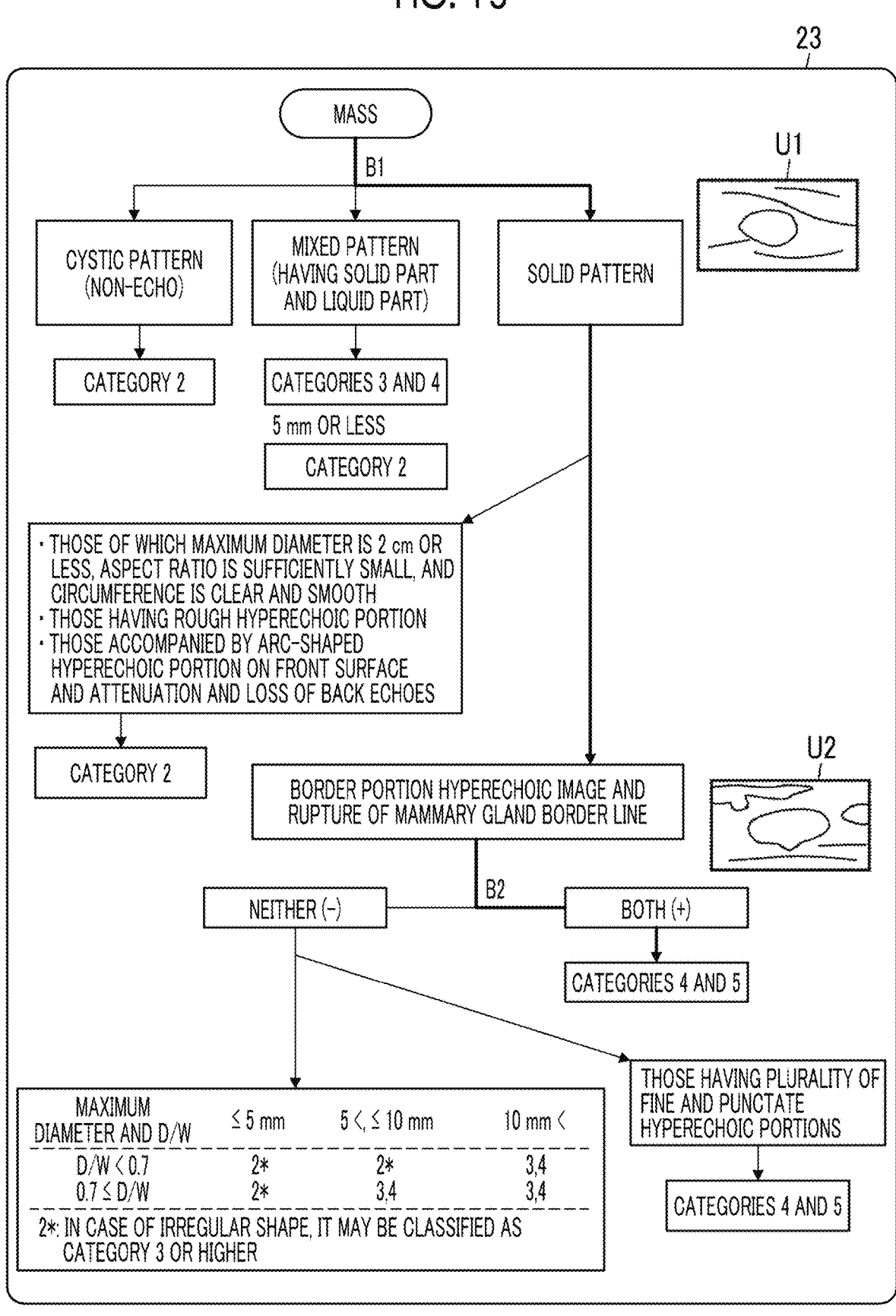
FIG. 13 is a diagram illustrating a determination procedure in which a route and a basis image are illustrated, according to the first embodiment.

In a case where the medical examination category of the lesion part is determined in this manner, the processing proceeds to Step S5, and as illustrated in FIG. 13, by the display controller 22, the determination procedure used in the determination of the medical examination category is displayed on the monitor 23, and further, the route in a case where the medical examination category is determined by the determination unit 27 and the basis image extracted by the extraction unit 26 are superimposed and displayed on the determination procedure.

The border of the lesion part determined by the identification unit 25 can be superimposed and displayed on the basis image.

In FIG. 13, the route in a case where the medical examination category is determined by the determination unit 27 is displayed by being emphasized by a thick line, so that it can be seen that the lesion part of the subject is determined to belong to the medical examination categories 4 and 5.

The route of the determination can be displayed by being emphasized by a line with a specific color without being limited to the thick line.

In the example illustrated in FIG. 13, in the first branch B1, it is determined that the lesion part corresponds to the solid pattern among three determination items of the cystic pattern, the mixed pattern, and the solid pattern, and the ultrasound image that best represents the determination is extracted by the extraction unit 26, and is displayed as a basis image U1 near the branch B1 in the determination procedure.

Similarly, in the branch B2, it is determined that the lesion part corresponds to at least one of the border portion hyperechoic image or the rupture of the mammary gland border line, and the ultrasound image that best represents the determination is extracted by the extraction unit 26, and is displayed as a basis image U2 near the branch B2 in the determination procedure.

In this manner, the characteristics of the lesion part for the determination item in the plurality of branches of the determination procedure are identified by the identification unit 25 on the basis of the plurality of ultrasound images in which the same lesion part of the subject is imaged, at least one ultrasound image contributing to the identification of the characteristics by the identification unit 25 is extracted as the basis image from the plurality of ultrasound images by the extraction unit 26, and the route in the determination procedure in a case of determining the medical examination category and the basis image extracted by the extraction unit 26 are displayed on the monitor 23 by the display controller 22. Therefore, it is possible to determine the medical examination category of the lesion part and accurately understand the basis of the determination from the plurality of ultrasound images regardless of the skill level of the user.

Figure 14:
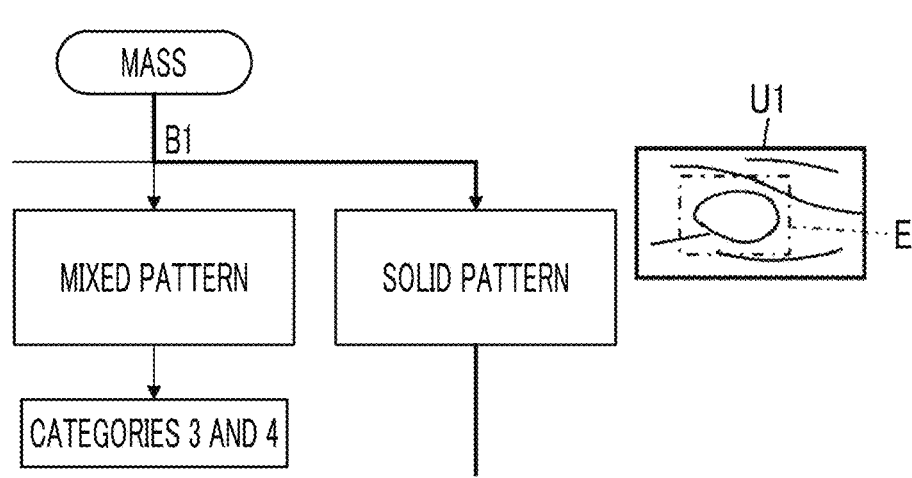
FIG. 14 is a diagram illustrating a part of a determination procedure in which a basis image including an enclosing line is displayed.

The extraction unit 26 can form an enclosing line to surround a portion contributing to the identification by the identification unit 25, in the basis image extracted from the plurality of ultrasound images on the basis of the identification result of the characteristics of the lesion part received from the identification unit 25, and an enclosing line E can be superimposed and displayed on the basis image U1 by the display controller 22 as illustrated in FIG. 14. Instead of the enclosing line E, a border line of the portion contributing to the identification may be superimposed and displayed on the basis image U1.

Figure 15:
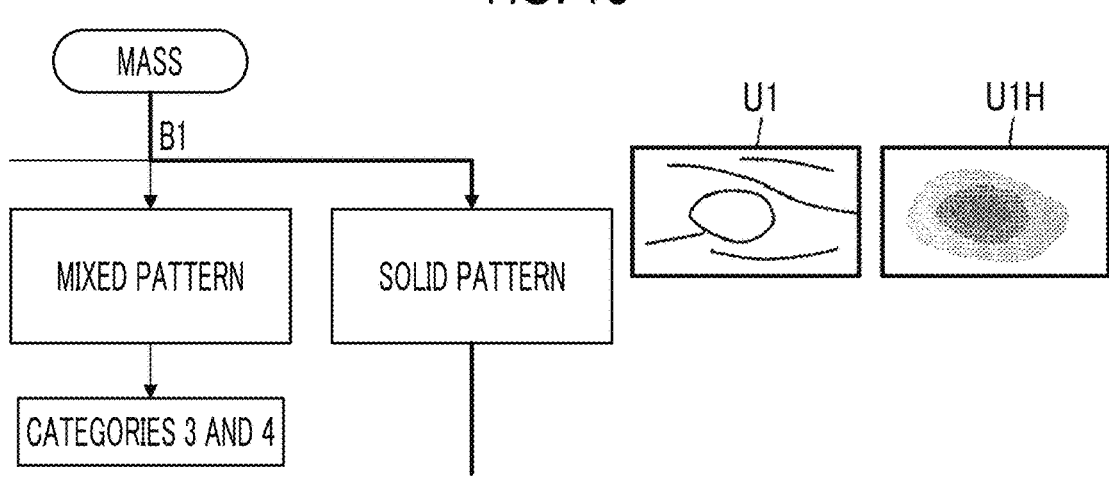
FIG. 15 is a diagram illustrating a part of a determination procedure in which a basis image and a heat map are displayed side by side.

Further, the extraction unit 26 may form a heat map in which a contribution rate of the portion contributing to the identification by the identification unit 25 is represented by color shading or color difference, on the basis of the basis image U1. As illustrated in FIG. 15, a heat map U1H can be displayed side by side with the basis image U1 on the monitor 23 by the display controller 22.

Figure 16:
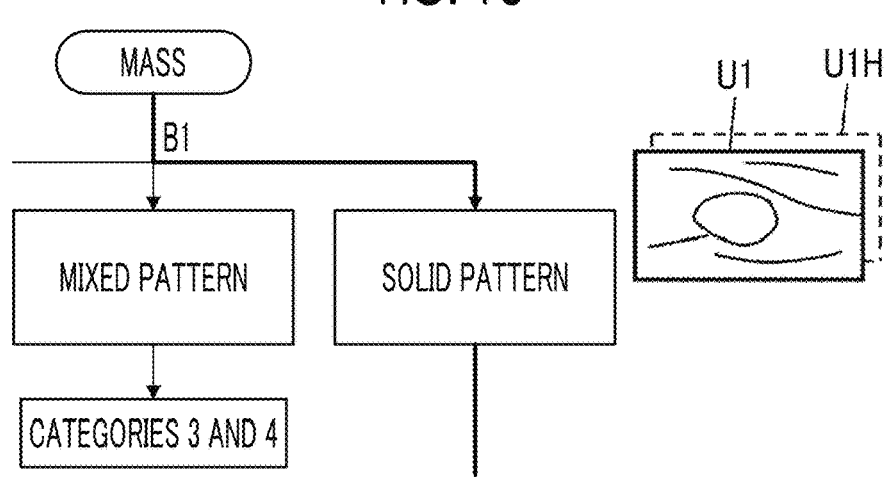
FIG. 16 is a diagram illustrating a part of a determination procedure in which a basis image and a heat map are sequentially displayed.

Instead of displaying the heat map U1H side by side with the basis image U1, the basis image U1 and the heat map U1H may be alternately displayed on the basis of the user's input operation via the input device 29, as illustrated in FIG. 16.

In this manner, by superimposing and displaying the enclosing line E on the basis image U1 or displaying the heat map U1H, the user can intuitively understand the portion contributing to the identification by the identification unit 25.

Figures 17, 18, 19:
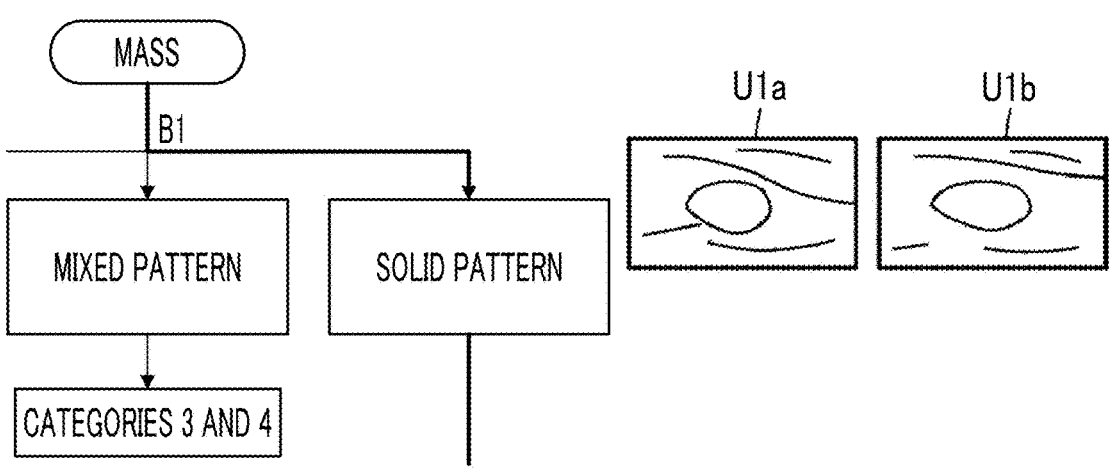
FIG. 17 is a diagram illustrating a part of a determination procedure in which a plurality of basis images are displayed side by side.
FIG. 18 is a diagram illustrating a part of a determination procedure in which a plurality of basis images are sequentially displayed.
FIG. 19 is a diagram illustrating a part of a determination procedure in which a size of a lesion part is displayed.

In each branch of the determination procedure, in a case where a plurality of basis images contributing to the identification by the identification unit 25 are extracted by the extraction unit 26, for example, as illustrated in FIG. 17, a plurality of corresponding basis images U1*a* and U1*b* can be displayed side by side near the branch.

Alternatively, a plurality of basis images extracted by the extraction unit 26 may be sequentially displayed on the monitor 23 on the basis of the user's input operation via the input device 29. In this case, for example, as illustrated in FIG. 18, a page number m/n indicating which of n basis images extracted by the extraction unit 26 is a basis image U1*m* that is currently being displayed, that is, indicating what number of the basis image U1*m*, can be displayed in an overlaid manner on the basis image U1*m*.

In a case where the plurality of basis images are sequentially displayed in this manner, even in a case where the monitor 23 does not have a large display space, the plurality of basis images can be displayed, and the page number is displayed in an overlaid manner so that the user can easily understand the plurality of basis images.

Further, the plurality of basis images may be sequentially and automatically displayed at certain time intervals without depending on the user's input operation.

As in the determination procedure illustrated in FIG. 4, the size of the lesion part is set as the determination item in a plurality of branches. Therefore, as illustrated in FIG. 19, the size of the lesion part measured by the identification unit 25, for example, the maximum diameter of the tumor and the aspect ratio of the mass can be displayed on the monitor 23 by being superimposed on the determination procedure.

It is configured such that the region of the tumor and the region of the mass are displayed on the image and the displayed regions can be modified by the user via the input device 29, and the identification unit 25 may correct the measurement value by measuring again the maximum diameter of the tumor and the aspect ratio of the mass on the basis of the modified regions. For example, in a case where the contour lines of the displayed regions are modified by the user, the measurement values of the maximum diameter of the tumor and the aspect ratio of the mass are corrected by the identification unit 25 on the basis of the modified region, and the medical examination category is determined again by the determination unit 27 on the basis of the corrected measurement values. The corrected maximum diameter of the tumor and the corrected aspect ratio of the mass are displayed on the monitor 23 by being superimposed on the determination procedure.

Further, the identification unit 25 can calculate a ratio of the region where the identified characteristics of the lesion part appear, to the total region of the lesion part for each set determination item of the determination procedure. For example, the identification unit 25 creates a three-dimensional image on the basis of the plurality of ultrasound images in which the same lesion part of the subject is imaged and which are analysis targets, and calculates the ratio of the region recognized as "rough" in the border portion of the lesion part to the entire region of the lesion part, for example. The calculated ratio can be displayed on the monitor 23 by being superimposed on the determination procedure as illustrated in FIG. 20.

Instead of creating the three-dimensional image, for example, the lengths of the rough portion and the other portions may be calculated for each frame, such as 2 cm of the rough portion and 8 cm of the other portions in the first frame, and 1.5 cm of the rough portion and 7 cm of the other portions in the second frame, and the ratio of the sum of the lengths of the rough portions in all the frames and the sum of the lengths of the other portions in all the frames may be calculated and displayed on the monitor 23.

As described above, the shape of the mass is classified according to whether the shape including the border hyperechoic portion has a "narrow part" and an "angulated part", and for example, the irregular shape as illustrated in FIG. 11 has both the "narrow part" and the "angulated part", but it is desirable to check the number of "narrow parts" and "angulated parts" in order to recognize that the mass has an irregular shape. Thus, the number of each of "narrow parts" and "angulated parts" of the lesion part can be calculated from the plurality of ultrasound images by the identification unit 25, and can be displayed on the monitor 23 by being superimposed on the determination procedure as illustrated in FIG. 21.

In this manner, by displaying the size of the lesion part, the ratio of the region where the identified characteristics of the lesion part appear to the entire region of the lesion part, and the number of "narrow parts" and "angulated parts" on the monitor 23 on the basis of the analysis by the identification unit 25, the user can understand in more detail the basis for the route selection in the plurality of branches of the determination procedure.

In the first embodiment described above, as illustrated in FIG. 12, the characteristics of the lesion part are identified for the plurality of ultrasound images by the identification unit 25 in Step S1, and the basis image contributing to the identification of the characteristics is extracted in Step S2, but the embodiments of the present invention are not limited thereto.

Figure 22:
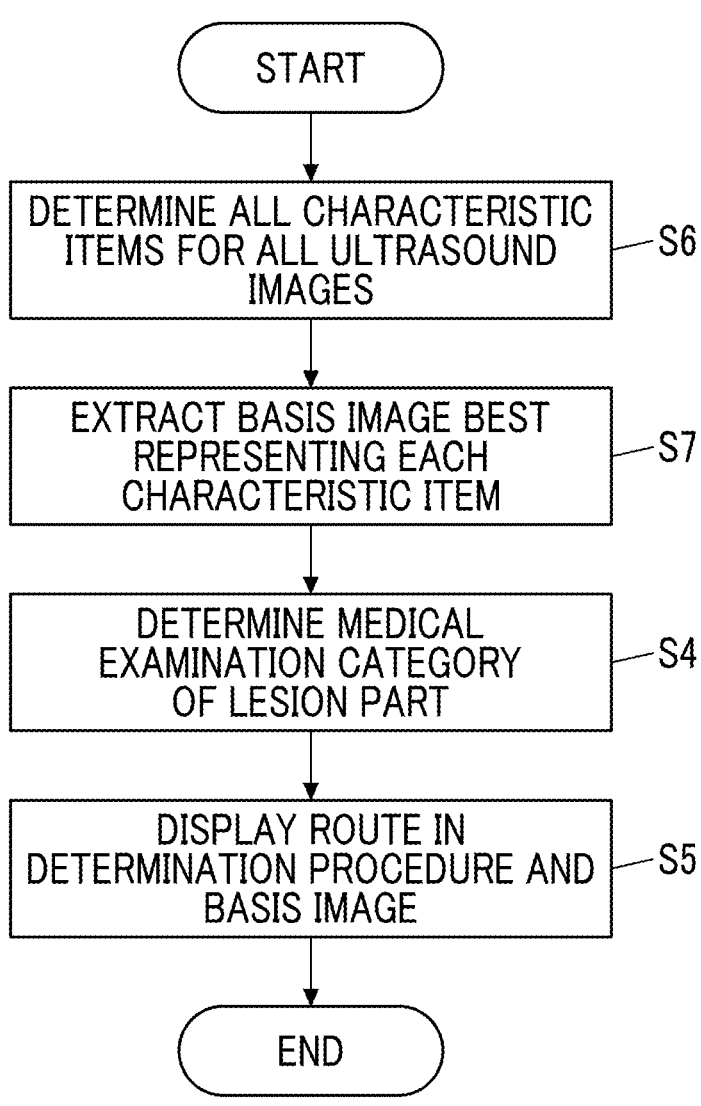
FIG. 22 is a flowchart illustrating an operation of a modification example of the first embodiment.

For example, as illustrated in the flowchart of FIG. 22, first, all the characteristic items stored in advance in the identification unit 25 may be determined for all the plurality of ultrasound images in Step S6, and along with the determination, in subsequent Step S7, at least one ultrasound image that best represents each characteristic item may be extracted as the basis image.

In this manner, in a case where the determination of all the characteristic items and the extraction of the basis image are performed, similar to the first embodiment, the processing proceeds to Step S4, the medical examination category of the lesion part is determined according to the determination procedure by the determination unit 27, and in Step S5, by the display controller 22, the determination procedure is displayed on the monitor 23, and the route in a case of determining the medical examination category and the basis image are superimposed and displayed on the determination procedure.

Second Embodiment

Figure 23:
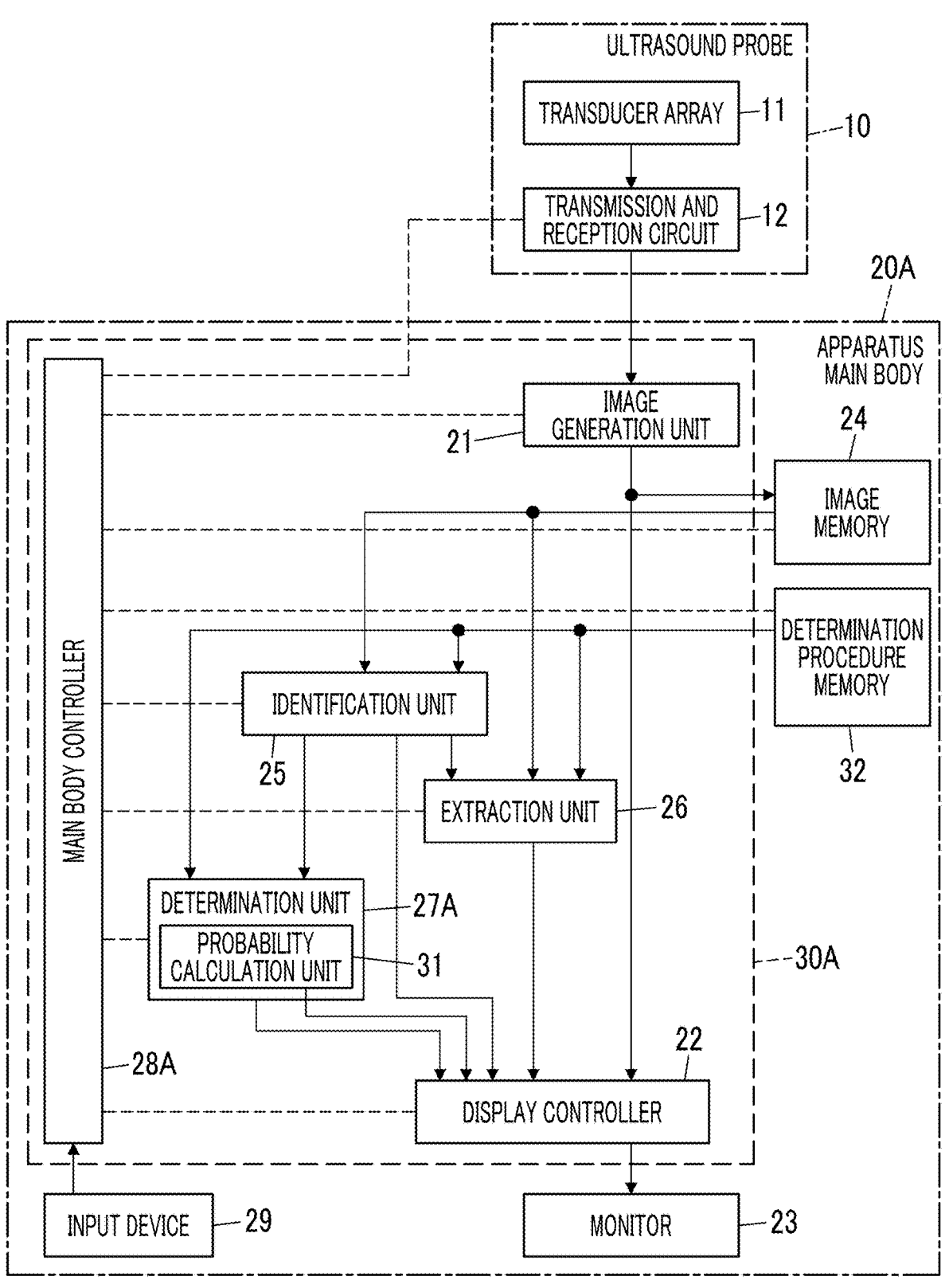
FIG. 23 is a block diagram illustrating a configuration of an ultrasound diagnostic apparatus according to a second embodiment.

FIG. 23 illustrates a configuration of an ultrasound diagnostic apparatus according to a second embodiment. The ultrasound diagnostic apparatus is configured by connecting an apparatus main body 20A to the ultrasound probe 10. The apparatus main body 20A uses a determination unit 27A to a main body controller 28A instead of the determination unit 27 and the main body controller 28 in the apparatus main body 20 of the ultrasound diagnostic apparatus according to the first embodiment illustrated in FIG. 1, and the other configuration of the apparatus main body 20A is the same as the apparatus main body 20 of the first embodiment.

The determination unit 27A includes a probability calculation unit 31 inside, and the probability calculation unit 31 is connected to the display controller 22.

The main body controller 28A is connected to the image generation unit 21, the display controller 22, the image memory 24, the identification unit 25, the extraction unit 26, the determination unit 27A, and the determination procedure memory 32, and the input device 29 is connected to the main body controller 28A. The transmission and reception circuit 12 of the ultrasound probe 10 is connected to the main body controller 28A.

The image generation unit 21, the display controller 22, the identification unit 25, the extraction unit 26, the determination unit 27A, and the main body controller 28A constitute a processor 30A.

In a case of performing the route selection of the determination procedure by applying the characteristics of the lesion part identified by the identification unit 25 to the determination item corresponding to each branch, the probability calculation unit 31 calculates the probability of route selection for each branch.

The calculation of the probability by the probability calculation unit 31 can be executed using a determination model trained using a machine learning technique such as deep learning, for example. The determination model is a trained model trained for the mammary gland region (segmentation) in the learning ultrasound images in which the breast is imaged, for example.

Figure 24:
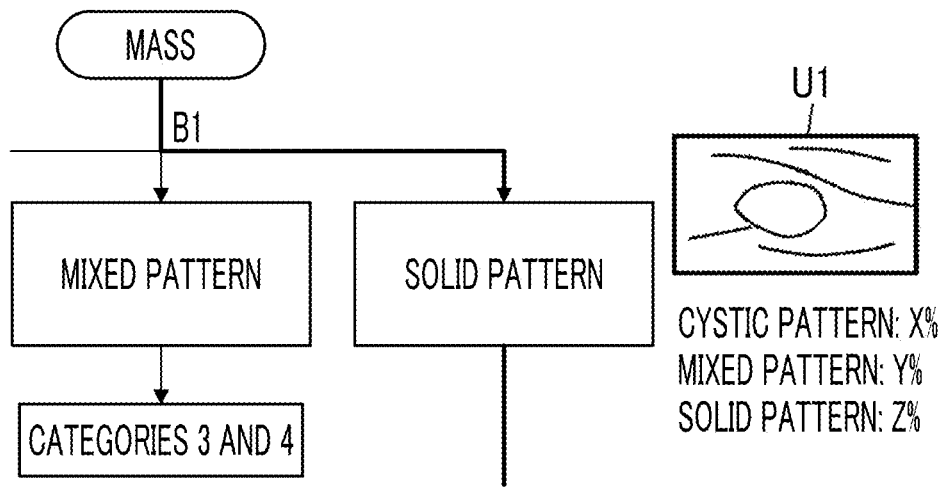
FIG. 24 is a diagram illustrating a part of a determination procedure in which a probability of route selection is displayed.

For example, the probability that the lesion part corresponds to each of three determination items of the cystic pattern, the mixed pattern, and the solid pattern in the first branch B1 of the determination procedure illustrated in FIG. 13 is calculated by the probability calculation unit 31. As illustrated in FIG. 24, a probability X % that the lesion part corresponds to the cystic pattern, a probability Y % that the lesion part corresponds to the mixed pattern, and a probability Z % that the lesion part corresponds to the solid pattern are displayed on the monitor 23 by being superimposed on the determination procedure by the display controller 22.

As a result, it is possible for the user to understand in more detail the basis for the route selection in each branch of the determination procedure.

For example, in a case where the lesion part corresponds to at least one of the border portion hyperechoic image or the rupture of the mammary gland border line in the branch B2 of the determination procedure illustrated in FIG. 13, it is determined that the lesion part belongs to the medical examination categories 4 and 5. In this manner, in a case where the lesion part corresponds to a plurality of medical examination categories in one branch, it is possible to determine which of the plurality of corresponding medical examination categories by comparing the probability of the route selection calculated by the probability calculation unit 31 with a predetermined threshold value.

For example, in a case where the probability that the lesion part corresponds to at least one of the border portion hyperechoic image or the rupture of the mammary gland border line in the branch B2 is equal to or less than the predetermined threshold value, it can be determined that the lesion part belongs to the medical examination category 4, and in a case where the probability is greater than the predetermined threshold value, it can be determined that the lesion part belongs to the medical examination category 5.

In the first and second embodiments described above, the ultrasound probe 10 has the transmission and reception circuit 12, but the apparatus main bodies 20 and 20A can include the transmission and reception circuit 12. Further, the apparatus main bodies 20 and 20A have the image generation unit 21, but the ultrasound probe 10 may have the image generation unit 21. Further, among the signal processing unit 41, the DSC 42, and the image processing unit 43 constituting the image generation unit 21 illustrated in FIG. 3, only the signal processing unit 41 may be provided in the ultrasound probe 10, and the apparatus main bodies 20 and 20A may have the DSC 42 and the image processing unit 43.

As the apparatus main bodies 20 and 20A in the first and second embodiments, a stationary type apparatus main body can be used, and a portable or handheld type compact apparatus main body can also be used.

In the first and second embodiments described above, the medical examination category of the lesion part in the mammary gland is determined according to the determination procedure stored in the determination procedure memory 32, but the embodiments of the present invention are not limited thereto, and by storing the determination procedure for determining the medical examination category regarding the thyroid gland in the determination procedure memory 32, similarly, the medical examination category of the lesion part in the thyroid gland can be determined according to the predetermined determination procedure having a plurality of branches.

Further, by storing the determination procedure for performing not only the determination of the medical examination category but also the determination of the diagnosis category in the determination procedure memory 32, the embodiments of the present invention can be similarly applied to the determination of the diagnosis category.

JABTS defines diagnosis categories I to V as follows.
Diagnosis category I: normal
Diagnosis category II: normal or inflammatory cell
Diagnosis category Ma: benign cell but malignancy cannot be ruled out
Diagnosis category Mb: high probability of malignancy but benignancy cannot be ruled out
Diagnosis category IV: suspicious of malignancy
Diagnosis category V: malignant By using the ultrasound diagnostic apparatus according to the embodiments of the present invention, similar to the medical examination category, it is possible to determine the diagnosis category of the lesion part in the mammary gland or thyroid gland from the plurality of ultrasound images and to accurately understand the basis for the determination regardless of the skill level of the user.

EXPLANATION OF REFERENCES

10: ultrasound probe
11: transducer array
12: transmission and reception circuit
13: pulser
14: amplification unit
15: AD conversion unit
16: beam former
20: apparatus main body
21: image generation unit
22: display controller
23: monitor
24: image memory
25: identification unit
26: extraction unit
27, 27A: determination unit
28, 28A: main body controller
29: input device
30A: processor
31: probability calculation unit
32: determination procedure memory
41: signal processing unit
42: DSC
43: image processing unit
B1, B2: branch
M: mass
N: tumor
H: border hyperechoic portion
L1, L2: maximum length
L3: maximum width
W: horizontal diameter
D: vertical diameter
U1, U1a, U1b, U1m, U2: basis image
E: enclosing line
U1H: heat map

What is claimed is:

1. An ultrasound diagnostic apparatus that determines a medical examination category or a diagnosis category of a lesion part according to a predetermined determination procedure having a plurality of branches, the ultrasound diagnostic apparatus comprising:
    a determination procedure memory that stores the predetermined determination procedure;
    a monitor; and
    a processor,
    wherein the processor is configured to:
        identify characteristics of the lesion part for a determination item for route selection in the plurality of branches of the predetermined determination procedure stored in the determination procedure memory on the basis of a plurality of ultrasound images in which the same lesion part is imaged,
        extract at least one ultrasound image contributing to identification of the characteristics in the plurality of branches of the predetermined determination procedure, from the plurality of ultrasound images as at least one basis image, at least two basis images extracted in at least two branches among the plurality of branches are different from each other,
        perform the route selection in the plurality of branches of the predetermined determination procedure by applying the identified characteristics to the determination item to determine the medical examination category or the diagnosis category of the lesion part,
        display the predetermined determination procedure on the monitor,
        display a route in the predetermined determination procedure in a case where the medical examination category or the diagnosis category is determined on the monitor, and
        display the basis image extracted in each of the plurality of branches of the predetermined determination procedure near the each of the plurality of branches on the predetermined determination procedure on the monitor,
    wherein the basis images different from each other are displayed near the at least two branches among the plurality of branches.

2. The ultrasound diagnostic apparatus according to claim 1,
    wherein the plurality of ultrasound images are images forming a video in which the lesion part is imaged.

3. The ultrasound diagnostic apparatus according to claim 2,
    wherein each of the plurality of ultrasound images is an image in which an entire or a part of the lesion part is imaged.

4. The ultrasound diagnostic apparatus according to claim 2,
    wherein the plurality of ultrasound images are a thinned-out image, an interpolated image, or a synthesized image from the images forming the video in which the lesion part is imaged.

5. The ultrasound diagnostic apparatus according to claim 2,
    wherein the processor forms an enclosing line surrounding a portion contributing to the identification of the characteristics, in the basis image, and superimposes and displays the enclosing line on the basis image.

6. The ultrasound diagnostic apparatus according to claim 2,
    wherein the processor forms a heat map in which a degree of how much a certain characteristic contributing to a diagnosis is represented by color shading or color difference, on the basis of the basis image, and displays the heat map on the monitor.

7. The ultrasound diagnostic apparatus according to claim 2,
    wherein in a case where a plurality of the basis images are extracted for one of the branches, the processor displays the plurality of basis images side by side on the monitor.

8. The ultrasound diagnostic apparatus according to claim 2,
    wherein in a case where a plurality of the basis images are extracted for one of the branches, the processor sequentially displays the plurality of basis images on the monitor on the basis of an instruction by the user.

9. The ultrasound diagnostic apparatus according to claim 8,
    wherein the processor displays a page number indicating which of the plurality of basis images is the basis image being displayed on the monitor in an overlaid manner on the basis image.

10. The ultrasound diagnostic apparatus according to claim 1,
    wherein each of the plurality of ultrasound images is an image in which an entire or a part of the lesion part is imaged.

11. The ultrasound diagnostic apparatus according to claim 1, wherein the processor forms an enclosing line surrounding a portion contributing to the identification of the characteristics, in the basis image, and superimposes and displays the enclosing line on the basis image.

12. The ultrasound diagnostic apparatus according to claim 1, wherein the processor forms a heat map in which a degree of how much a certain characteristic contributing to a diagnosis is represented by color shading or color difference, on the basis of the basis image, and displays the heat map on the monitor.

13. The ultrasound diagnostic apparatus according to claim 1, wherein in a case where a plurality of the basis images are extracted for one of the branches, the processor displays the plurality of basis images side by side on the monitor.

14. The ultrasound diagnostic apparatus according to claim 1, wherein in a case where a plurality of the basis images are extracted for one of the branches, the processor sequentially displays the plurality of basis images on the monitor on the basis of an instruction by the user.

15. The ultrasound diagnostic apparatus according to claim 1, wherein the processor measures a size of the lesion part, and displays the measured size on the monitor.

16. The ultrasound diagnostic apparatus according to claim 1, wherein the processor calculates a ratio of a region where the identified characteristics appear to an entire region of the lesion part for each determination item, and displays the calculated ratio on the monitor.

17. The ultrasound diagnostic apparatus according to claim 1, wherein the processor calculates a probability of the route selection in the plurality of branches of the predetermined determination procedure on the basis of the characteristics of the lesion part, and displays the calculated probability on the monitor.

18. The ultrasound diagnostic apparatus according to claim 17, wherein in a case where a plurality of the medical examination categories or the diagnosis categories correspond to any one of the plurality of branches of the predetermined determination procedure, the processor compares the calculated probability with a predetermined threshold value to determine the medical examination category or the diagnosis category of the lesion part.

19. The ultrasound diagnostic apparatus according to claim 1, further comprising:

an ultrasound probe, wherein the processor generates the plurality of ultrasound images in which the same lesion part is imaged, by performing transmission and reception of ultrasound beams with respect to a subject using the ultrasound probe.

20. A control method of an ultrasound diagnostic apparatus that determines a medical examination category or a diagnosis category of a lesion part according to a predetermined determination procedure having a plurality of branches, the control method comprising:

a step of identifying characteristics of the lesion part for a determination item for route selection in the plurality of branches of the predetermined determination procedure on the basis of a plurality of ultrasound images in which the same lesion part is imaged;

a step of extracting at least one ultrasound image contributing to identification of the characteristics in the plurality of branches of the predetermined determination procedure, from the plurality of ultrasound images as at least one basis image, at least two basis images extracted in at least two branches among the plurality of branches are different from each other;

a step of performing the route selection in the plurality of branches of the predetermined determination procedure by applying the identified characteristics to the determination item to determine the medical examination category or the diagnosis category of the lesion part;

a step of displaying the predetermined determination procedure on a monitor;

a step of displaying a route in the predetermined determination procedure in a case where the medical examination category or the diagnosis category is determined on the monitor; and a step of displaying the basis image extracted in each of the plurality of branches of the predetermined determination procedure near the each of the plurality of branches on the predetermined determination procedure on the monitor, wherein the basis images different from each other are displayed near the at least two branches among the plurality of branches.

* * * * *